United States Patent [19]

Yoshido et al.

[11] Patent Number: 4,994,102

[45] Date of Patent: Feb. 19, 1991

[54] HERBICIDAL COMPOSITION

[75] Inventors: Ryo Yoshido, Misawa; Yoshihiro Mano, Toyonaka; Hideyuki Shibata, Takarazuka, all of Japan

[73] Assignee: Sumitomo Chemical Co., Ltd., Osaka, Japan

[21] Appl. No.: 374,867

[22] Filed: Jul. 3, 1989

[30] Foreign Application Priority Data

Jul. 8, 1988 [JP] Japan .................................. 63-171346

[51] Int. Cl.$^5$ .................... A01N 57/04; A01N 43/38
[52] U.S. Cl. ............................................. 71/86; 71/96
[58] Field of Search ........................................ 71/86, 96

[56] References Cited
U.S. PATENT DOCUMENTS

| | | | |
|---|---|---|---|
| 3,799,758 | 3/1974 | Franz | 71/86 |
| 3,929,450 | 12/1975 | Hamm et al. | 71/86 |
| 4,445,927 | 5/1984 | Gimesi et al. | 71/86 |
| 4,612,034 | 9/1986 | Kruger et al. | 71/86 |
| 4,640,707 | 2/1987 | Nagano et al. | 71/96 |

OTHER PUBLICATIONS

"The pesticide Manual" A World Compendium, Eighth Edition, The British Crop Protection Council, pp. 449-450.

*Primary Examiner*—Glennon H. Hollrah
*Assistant Examiner*—Mark Clardy
*Attorney, Agent, or Firm*—Birch, Stewart, Kolasch & Birch

[57] ABSTRACT

A herbicidal composition which comprises as the active ingredients (a) 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione and (b) N-(phosphonomethyl)glycine or its salt (glyphosate), and an inert carrier or diluent. The composition exerts a synergistic herbicidal activity.

5 Claims, 1 Drawing Sheet

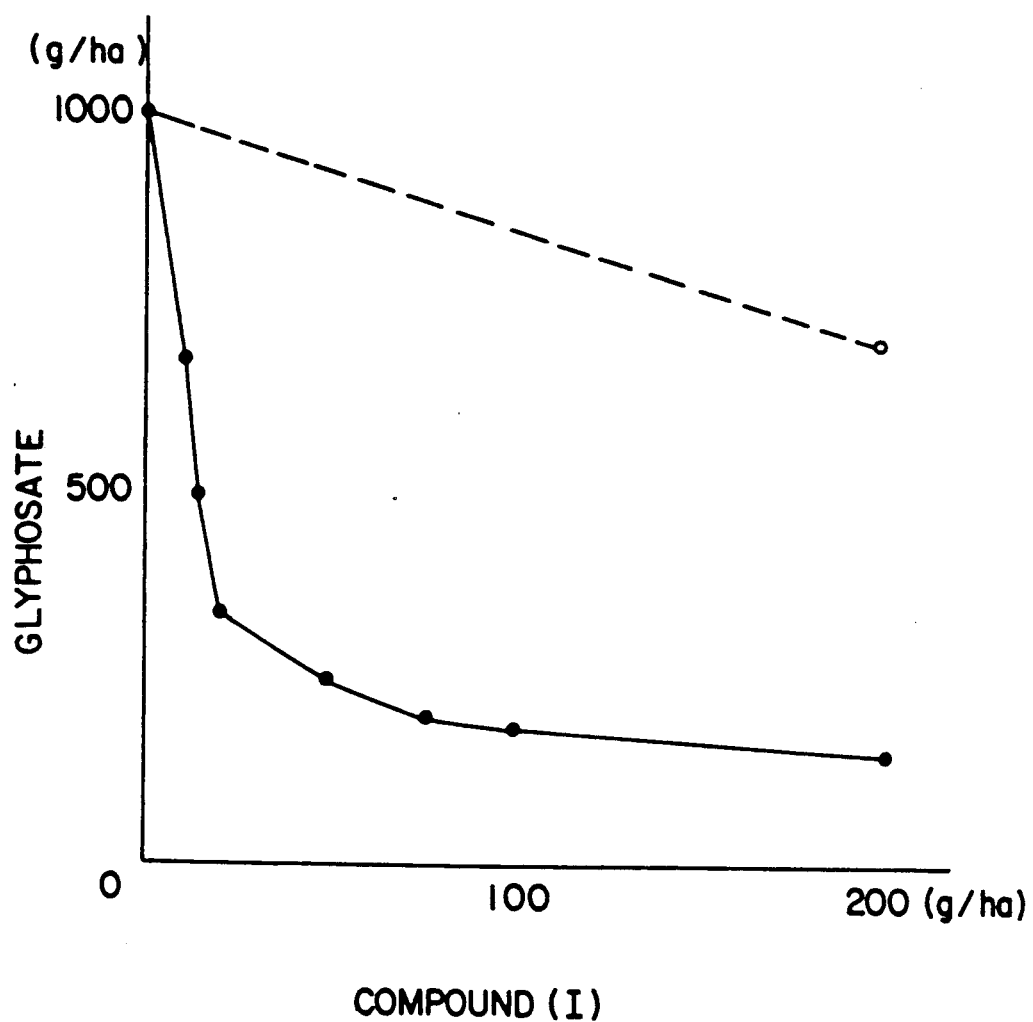

HERBICIDAL COMPOSITION

The present invention relates to a herbicidal composition. More particularly, it relates to a herbicidal composition comprising as the active ingredients (a) 2-[7-fluoro-3,4-dihydro-3-oxo-4-(2-propynyl) -2H-1,4-benzoxazin-6-yl 4,5,6,7-tetrahydro-1H-isoindole-1,3(2H)-dione (hereinafter referred to as "Compound (I)") of the formula:

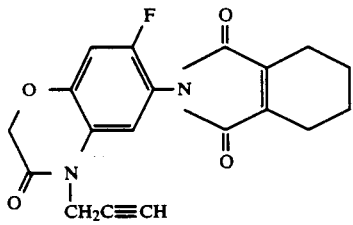

and (b) N-(phosphonomethyl)glycine of the formula:

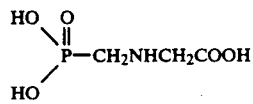

or its salt (hereinafter referred to as "glyphosate"), which exerts a highly enhanced herbicidal activity against a wide variety of weeds.

In recent years, there have been used a great number of chemicals having herbicidal activities in order to exterminate or control undesired vegetation of weeds in agricultural and non-agricultural fields. Since, however, weeds are diversified in kinds and grow over a long period of time, the herbicidal effects of conventional herbicidal agents are restricted in general. Under the circumstances, the appearance of any herbicidal agent exerting a strong herbicidal activity as well as a broad herbicidal spectrum over a wide variety of weeds has been highly demanded.

Glyphosate is known as a herbicide applicable before planting or plowing, but it takes a relatively long time until the complete extermination of undesired weeds after its application, e.g. about 10 days or more. If this period can be shortened, it would be a great advantage for farmers to practice the subsequent farm works such as planting and plowing.

As a result of the extensive study, it has now been found that the associated use of Compound (I) with glyphosate as the active ingredients produces a highly enhanced herbicidal activity against a wide variety of weeds in agricultural and non-agricultural fields. In comparison with the sole use of each of said active ingredients, enhancement of the herbicidal potency on such associated use is remarkable so that the active ingredients may be applied in smaller dosages. Further, the weed-control spectrum is greatly enlarged. Furthermore, in comparison with the sole use of glyphosate, the herbicidal effect starts to exert much quickly, e.g. within one or two days after the application. Accordingly, the complete exterminaton of weeds, though it varies depending on the species, is realized almost within one week. Thus, a clear and definite synergistic effect is observed in said associated use.

The herbicidal composition of the invention can exterminate or control a variety of weeds, of which typical examples are broad-leaved weeds such as wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), slender amaranth (*Amaranthus gracilis*), radish (*Raphanus sativus*), wild mustard (*Sinapis arvensis*), shepherdspurse (*Capsella bursa-pastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Pharbitis purpurea*), field bindweed . (*Convolvulus arvensis*), flexuous bittercress (*Cardamine flexuosa*), prickly sow-thistle (*Sonchus asper*), fleabane . (*Erigeron sumatrensis*), purple deadnettle (*Lamium purpureum*), henbit (*Lamium amplexicaure*), jimsonweed (*Datura stramonium*), black nightshade (*Solanum nigrum*), persian speedwell (*Veronica persica*), common cocklebur (*Xanthium strumarium*), common sunflower (*Helianthus annuus*), scentless chamomile (*Matricaria perforata*), corn marigold (*Chrysanthemum segetum*), curly dock (*Rumex crispus*) and Japanese mugwort (*Artemisia princeps*); graminaceous weeds such as japanese millet (*Echinochloa frumentacea*), barnyardgrass, (*Echinochloa crusgalli*), green foxtail (*Setaria viridis*), water foxtail (*Alopecurus geniculatus*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*), bluestem (*Agropyron tsukushiense*) and bermudagrass (*Cynodon dactylon*); commnelinaceous weeds such as asiatic dayflower (*Commelina communis*); cyperaceous weeds such as rice flatsedge (*Cyperus iria*) and purple nutsedge (*Cyperus rotundus*), etc.

Compound (I) is known to exert a herbicidal activity (U.S. Pat. No. 4,640,707). Glyphosate is described in C. R. Worthing et al: The Pesticide Mannual, 8th Ed., page 449 (1987) published by The British Crop Protection Council, and it is usable as such or in an agriculturally acceptable salt form (e.g. isopropylamine salt). However, the associated use of Compound (I) with glyphosate has never been attempted, and the production of synergism on the associated use has never been expected.

The proportion of Compound (I) as the component (a) and glyphosate as the component (b) in the composition of the invention may vary in a considerably broad range and is usually within a range of 1:0.5 to 1:100 by weight, preferably of 1:1 to 1:70 by weight, more preferably of 1:2.5 to 1:40 by weight.

In addition to the active ingredients as above, the composition may contain a solid or liquid carrier or diluent. Any surface active or auxiliary agent may be also contained therein. Thus, the compositon may be formulated in any conventional preparation form such as wettable powder or suspension. The total content of the active ingredients, i.e. Compound (I) and glyphosate, may be from 1 to 90% by weight, preferably from 2 to 80% by weight.

As the solid carrier or diluent, there may be used kaolin clay, attapulgite clay, bentonite, terra alba, pyrophyllite, talc, diatomaceous earth, calcite, wallnut-shell powder, urea, ammonium sulfate, synthetic hydrated silica, etc. Examples of the liquid carrier or diluent are water, etc.

The surface active agent used for dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the composition are illustratively shown in the following Formulation Examples wherein part(s) are by weight.

FORMULATION EXAMPLE 1

One part of Compound (I), 50 parts of glyphosate, 3 parts of calcium ligninsulfonate, 2 parts of sodium laurylsulfate and 44 parts of synthetic hydrated silica are mixed well and pulverized to obtain a wettable powder.

FORMULATION EXAMPLE 2

One part of Compound (I), 20 parts of glyphosate, 3 parts of polyoxyethylene sorbitan monooleate, 3 parts of CMC and 73 parts of water are mixed and pulverized until the particle size becomes less than 5 microns to make a suspension.

FORMULATION EXAMPLE 3

Twenty-five parts of Compound (I), 25 parts of glyphosate, 3 parts of calcium ligninsulfonate, 2 parts of sodium laurylsulfate and 45 parts of synthetic hydrated silica are mixed well and pulverized to obtain a wettable powder.

FORMULATION EXAMPLE 4

0.7 part of Compound (I), 49 parts of glyphosate, 3 parts of calcium ligninsulfonate, 2 parts of sodium laurylsulfate and 45.3 parts of synthetic hydrated silica are mixed well and pulverized to obtain a wettable powder.

FORMULATION EXAMPLE 5

1.5 parts of Compound (I), 50 parts of glyphosate, 3 parts of calcium ligninsulfonate, 2 parts of sodium laurylsulfate and 43.5 parts of synthetic hydrated silica are mixed well and pulverized to obtain a wettable powder.

FORMULATION EXAMPLE 6

0.4 part of Compound (I), 1.6 parts of glyphosate, 1 part of polyoxyethylene sorbitan monooleate, 1 part of CMC and 96 parts of water are mixed and pulverized until the particle size becomes less than 5 microns to make a suspension.

FORMULATION EXAMPLE 7

0.4 Part of Compound (I), 10 parts of "Sorpol 5050" ® (an anionic surface active agent manufactured by Toho Yakuhin Kogyo K.K.; containing 50% dialkylsulfosuccinate), 4 parts of sodium ligninsulfonate, 5 parts of synthetic hydrated silica, 79 parts of clay are mixed well. 1.6 Parts of glyphosate are added thereto, and the mixture is pulverized well to obtain a wettable powder.

A composition comprising Compound (I) and glyphosate thus formulated is useful for post-emergence control of undesired weeds by foliar treatment, etc. The foliar treatment may be effected by spraying the composition containing Compound (I) and glyphosate over the top of plants. The direct application may also be adopted.

In order to improve the herbicidal activity, the composition may be used with other herbicides. Besides, it may be used in combination with insecticides, acaricides, nematocides, fungicides, plant growth regulators, fertilizers, soil improvers, etc.

The composition of the invention is widely used as the herbicide applicable in plowed field, non-cropping land, orchards, pasture land, lawn, forest, non-agricultural fields, etc.

The dosage of the active ingredients may vary depending on prevailing weather conditions, soil involved, formulation used, mixing proportion of each active ingredient, crop and weed species, etc. In general, however, the total amount of Compound (I) and glyphosate may be within a range of about 100 to 5000 grams per hectare, preferably within a range of about 200 to 3000 grams per hectare.

The composition in the form of wettable powder, suspension or the like is normally diluted with water and applied at a volume of 100 to 1000 liters per hectare to the area where the extermination of weeds is desired. The dilution may further include, in addition to the above mentioned surface active agent, any spreading or auxiliary agent such as polyoxyethylene resin acid esters, ligninsulfonates, abietic acid, dinaphthylmethanedisulfonates, paraffin or petroleum oil.

The herbicidal activity of the composition of the invention will be explained in further detail with reference to the following Test Examples. Further, throughout Test Examples, glyphosate was used in the form of an isopropylamine salt.

TEST EXAMPLE 1

Sandy upland field soil was filled in concrete pots (50×50×30 cm), and seeds of downy brome, wild oats, water foxtail, catchweed bedstraw, wild buckwheat and flexuous bittercress were sowed therein and cultivated outdoors for 40 days. A designed amount of the composition in the form of a wettable powder formulated according to Formulation Example 1, 3, 4 or 5 was diluted with water containing a 0.2% (v/v) surfactant (containing dialkylsulfosuccinate) and sprayed to the foliage of the test plants at a spray volume of 500 liters per hectare by the aid of a small hand sprayer. Three and nineteen days thereafter, the herbicidal activity was observed. The results are shown in Tables 1 and 2 wherein the herbicidal activity was observed visually and classified into numerals ranging from 0 (no control) to 10 (complete death). At the time of treatment, the weeds were at 1 to 3-leaf stage and 4 to 8 cm in height.

TABLE 1

| Test Compound | Dosage (g/ha) | Herbicidal activity 3 days after the treatment | | | | | |
|---|---|---|---|---|---|---|---|
| | | Downy brome | Wild oats | Water foxtail | Catchweed bedstraw | Wild buckwheat | Flexuous bittercress |
| Compound (I) | 10 | 2.5 | 4 | 3.5 | 8 | 8.5 | 8 |

TABLE 1-continued

| Test Compound | Dosage (g/ha) | Herbicidal activity 3 days after the treatment | | | | | |
|---|---|---|---|---|---|---|---|
| | | Downy brome | Wild oats | Water foxtail | Catchweed bedstraw | Wild buckwheat | Flexuous bittercress |
| | 30 | 4 | 3.5 | 6 | 8.5 | 9 | 9 |
| | 100 | 5 | 5.5 | 7 | 9 | 9 | 9 |
| | 1100 | 7 | 8.5 | 9 | 9 | 10 | 9 |
| Glyphosate | 500 | 2 | 2.5 | 3 | 1.5 | 2.5 | 3 |
| | 1000 | 4 | 5 | 4 | 4 | 4.5 | 5 |
| | 2000 | 4 | 5 | 4.5 | 4 | 4.5 | 5.5 |
| Compound (I) | 10 + 500 | 9 | 9.5 | 9 | 9 | 9.5 | 9.5 |
| + | 10 + 1000 | 9.5 | 10 | 9.5 | 9 | 10 | 10 |
| Glyphosate | 30 + 500 | 9 | 10 | 10 | 9.5 | 9.5 | 10 |
| | 30 + 1000 | 9.5 | 10 | 10 | 9.5 | 10 | 10 |
| | 100 + 500 | 9.5 | 10 | 10 | 9.5 | 9.5 | 10 |
| | 100 + 1000 | 9.5 | 10 | 10 | 10 | 10 | 10 |

TABLE 2

| Test Compound | Dosage (g/ha) | Herbicidal activity 19 days after the treatment | | | | | |
|---|---|---|---|---|---|---|---|
| | | Downy brome | Wild oats | Water foxtail | Catchweed bedstraw | Wild buckwheat | Flexuous bittercress |
| Compound (I) | 10 | 3 | 4 | 4 | 9 | 10 | 9.5 |
| | 30 | 4.5 | 4 | 6 | 9.5 | 10 | 10 |
| | 100 | 6 | 5.5 | 8 | 9.8 | 10 | 10 |
| | 1100 | 7 | 9.5 | 9.8 | 10 | 10 | 10 |
| Glyphosate | 500 | 6 | 6 | 7 | 0.5 | 1.5 | 5 |
| | 1000 | 9 | 9.3 | 9 | 5.5 | 5.5 | 8 |
| | 2000 | 10 | 10 | 9.8 | 8 | 8.8 | 9.3 |
| Compound (I) | 10 + 500 | 9.5 | 10 | 10 | 9 | 10 | 10 |
| + | 10 + 1000 | 9.8 | 10 | 10 | 9.8 | 10 | 10 |
| Glyphosate | 30 + 500 | 9.8 | 10 | 10 | 10 | 10 | 10 |
| | 30 + 1000 | 10 | 10 | 10 | 10 | 10 | 10 |
| | 100 + 500 | 10 | 10 | 10 | 10 | 10 | 10 |
| | 100 + 1000 | 10 | 10 | 10 | 10 | 10 | 10 |

TEST EXAMPLE 2

Pear fields where large crabgrass, barnyardgrass, prickly sow-thistle, fleabane, ladysthumb and slender amaranth germed spontaneously were plotted with three replicates (each plot being 2.8×3.6 m). A designed amount of the composition in the form of a wettable powder formulated according to Formulation Example 1, 3, 4 or 5 was diluted with water containing a 0.2% (v/v) surfactant (containing dialkylsulfosuccinate) and sprayed to the foliage of the test plants at a spray volume of 1000 liters per hectare by the aid of a small hand sprayer. Sixteen days thereafter, the herbididal activity was observed. At the time of treatment, large crabgrass, barnyardgrass, prickly sow-thistle, fleabane, ladysthum and slender amaranth were in 5 to 10, 30 to 40, 30 to 40, 5 to 10, 40 to 70 and 5 to 10 cm in height, respectively. The results are shown in Table 3 wherein the herbicidal activity was evaluated according to the same manner as in Test Example 1.

TEST EXAMPLE 3

Sandy upland field soil was filled in Wagner pots (inner diameter, 16 cm; height, 19 cm), and seeds of downy brome were sowed therein and cultivated outdoors for 40 days. A designed amount of the composition in the form of a wettable powder formulated according to Formulation Example 1, 3, 4 or 5 was diluted with water containing a 0.2% (v/v) surfactant (containing 80% polyoxyethylene dodecyl ether) and sprayed to the foliage of the test plant at a spray volume of 500 liters per hectare by the aid of a small hand sprayer. Twenty days thereafter, a growth control percentage was observed, and the results are shown in Table 4. At the time of treatment, the test plant was at 3-leaf stage and 10 cm in height. The growth control percentage (%) was determined by weighing the aerial parts of the test plants (fresh weight) and making calculation according to the following equation:

TABLE 3

| Test Compound | Dosage (g/ha) | Herbicidal activity | | | | | |
|---|---|---|---|---|---|---|---|
| | | Large crabgrass | Barnyardgrass | Prickly sow-thistle | Fleabane | Ladysthum | Slender amaranth |
| Compound (I) | 30 | 4.3 | 3.7 | 6 | 4 | 8.7 | 7.3 |
| | 60 | 7 | 5.3 | 9 | 6.3 | 9 | 9 |
| | 860 | 9 | 7 | 10 | 9.7 | 9.7 | 10 |
| Glyphosate | 800 | 8.3 | 8 | 7 | 7 | 4 | 7 |
| | 1200 | 9 | 9 | 8 | 7.7 | 6 | 10 |
| Compound (I) | 30 + 800 | 9.3 | 9.7 | 10 | 9.7 | 10 | 10 |
| + | 60 + 800 | 10 | 10 | 10 | 10 | 10 | 10 |
| Glyphosate | | | | | | | |

$$\text{Growth controlling percentage (\%)} = \left\{ 1 - \frac{\text{Fresh weight of test plant in treated plot}}{\text{Fresh weight of test plant in untreated plot}} \right\} \times 100$$

TABLE 4

| | | Compound (I) (g/ha) | | | | | | |
|---|---|---|---|---|---|---|---|---|
| | | 0 | 10 | 20 | 50 | 100 | 200 | 500 | 1000 |
| Glyphosate (g/ha) | 0 | 0 | 7 | 13 | 25 | 49 | 66 | 84 | 99 |
| | 100 | 20 | 33 | 40 | 52 | 75 | 82 | | |
| | 200 | 44 | 60 | 83 | 87 | 92 | 96 | | |
| | 500 | 71 | 86 | 95 | 100 | 100 | 100 | | |
| | 1000 | 90 | 95 | 100 | 100 | 100 | 100 | | |
| | 2000 | 100 | 100 | 100 | 100 | 100 | 100 | | |

The results in Test Example 3 were analyzed according to the isobole (i.e. equivalent efficacy line) method [Vol. 3, Herbicides, pages 109–111 (1981) in "Noyaku Jikkenho"] (Methods in Pesticide Science) edited by Junichi Fukami et al., Soft Science Inc., Tokyo) based on the Tammes's method [Tammes, P. M. L.: Neth. J. Plant Path., 70, 73–80 (1964)]. Namely, several combinations of the compositions having different mixing ratios of Compound (I) and glyphosate but exerting the same level of growth control effect, for example, 90% growth control, were plotted in a graph so as to readily determine a synergistic effect, an arithmetic effect or a competitive effect. In case of exhibiting the synergistic effect, the equivalent efficacy line as plotted is shown below the arithmetic efficacy line.

Explaining further in detail with reference to the accompanying drawings, FIG. 1 wherein the ordinate indicates the dosage of glyphosate and the abscissa indicates the dosage of Compound (I), the equivalent efficacy line (i.e. solid line) of 90% growth control of downy brome is located under the arithmetic efficacy line (i.e. dotted line), from which it is understood that the associated use of Compound (I) and glyphosate in a certain mixing ratio produces the synergistic effect.

What is claimed is:

1. A herbicidal composition which comprises as the active ingredients (1) 2-{7-fluoro-3,4-dihydro-3-oxo-4-(2-propynyl)-2H-1,4-benzoxazin -6-yl}-4,5,6,7-tetrahydro-1H-isoindole-1,3(2H)-dione and (b) N-(phosphonomethyl)-glycine or its salt, and an inert carrier or diluent, wherein the weight proportion of the components (a) and (b) is from 1:1 to 1:70.

2. The composition according to claim 1, wherein the weight proportion of the components (a) and (b) is from 1:2.5 to 1:40.

3. A method for controlling downy frome which comprises applying a herbicidally effective amount of the composition according to claim 1 to weeds.

4. The method according to claim 3, wherein the total amount of the components (a) and (b) is from 200 to 3000 grams per hectare.

5. The method according to claim 3, wherein the weight proportion of the components (a) and (b) is from 1:2.5 to 1:40.

* * * * *

UNITED STATES PATENT AND TRADEMARK OFFICE
CERTIFICATE OF CORRECTION

PATENT NO. : 4,994,102
DATED : Feb. 19, 1991
INVENTOR(S) : Ryo YOSHIDA, Yoshihiro MANO and Hideyuki SHIBATA It is certified that error appears in the above-identified patent and that said Letters Patent is hereby corrected as shown below:

On the title page, item [75]:
Change the family name of the first listed inventor from "Yoshido" to --Yoshida--.

Signed and Sealed this

Sixth Day of October, 1992

Attest:

*Attesting Officer*

DOUGLAS B. COMER

*Acting Commissioner of Patents and Trademarks*